United States Patent [19]

Welch et al.

[11] Patent Number: 4,962,111

[45] Date of Patent: Oct. 9, 1990

[54] PYRAZINOIC ACID ESTERS AS ANTITUBERCULOSIS AGENTS

[75] Inventors: John T. Welch, Albany; Michael H. Cynamon, Syracuse, both of N.Y.

[73] Assignee: The Research Foundation of State University of New York, Albany, N.Y.

[21] Appl. No.: 364,067

[22] Filed: Jun. 8, 1989

[51] Int. Cl.$^5$ .................. A61K 31/495; C07D 241/14; C07D 241/16; C07D 241/18

[52] U.S. Cl. .................................... 514/255; 514/924; 544/406

[58] Field of Search ................ 544/405, 406; 514/252, 514/255, 924

[56] References Cited

U.S. PATENT DOCUMENTS

| | | | |
|---|---|---|---|
| 2,646,431 | 7/1953 | Dalalian | 544/406 |
| 2,677,641 | 5/1954 | Williams et al. | 514/255 |
| 4,051,245 | 9/1977 | Ambrogi et al. | 544/406 |
| 4,141,977 | 2/1979 | Yu et al. | 544/406 |

FOREIGN PATENT DOCUMENTS 1361967  7/1974  United Kingdom ................ 544/406

OTHER PUBLICATIONS

Kushner, S. et al., Experimental Chemotherapy of Tuberculosis., II., The Synthesis of Pyrazinamides and Related Compounds, J. Am. Chem. Soc., 74:3617–3621 (1952).

Solomons, I. A., and Spoerri, P. E., Esters of Pyrazinoic and Pyrazine-2,3-Dicarboxylic acids, J. Am. Chem. Soc., 75:679–681 (1953).

Kushner, S. et al., Experimental Chemotherapy of Tuberculosis., III, Ethyl Mercaptan and Related Compounds in Tuberculosis, J. Am. Chem. Soc., 77:1152–1155 (1954).

Brown, H.D. et al., The Antituberculosis Activity of Some Ethylmercapto Compounds, J. Am. Chem. Soc., 76:3860 (1954).

Suzuki, M., et al., Takamine Kenyusho Nempo 10:19–23 (1958), The Annual Report of Takamine Laboratory, vol. X.

Lewis, A. And Shepard, R. G. Antimycobacterial Agents. in Alfred Burger, ed. Medicinal Chemistry Part I., 409–491 (1970).

Ul'Yanova et al, Chem. Abst. 79-125379t (1973).

*Primary Examiner*—Cecilia Shen
*Attorney, Agent, or Firm*—Heslin & Rothenberg

[57] ABSTRACT

Pyrazinoic esters have been prepared. Compounds of this group are effective against mycobacteria including Mycobacteria tuberculosis, pyrazinamide-resistant Mycobacteria tuberculosis, Mycobacteria bovis and Mycobacteria kansasii.

24 Claims, No Drawings

PYRAZINOIC ACID ESTERS AS ANTITUBERCULOSIS AGENTS

Statement of Rights under Federally-sponsored Research

This invention was made with government support under CHE 8520875 awarded by The National Science Foundation. The government has certain rights in the invention.

TECHNICAL FIELD

This invention relates generally to the field of therapeutic agents for the treatment of tuberculosis.

BACKGROUND OF THE INVENTION

The goal of chemotherapy of mycobacterial infections is to stop the worsening of the disease, to convert secretions to a noninfectious state by killing the bacilli if possible, and to allow healing of gross pathological damage. Tuberculosis is not cured by present drugs in the strict sense of the word, even though relapse rates can be minimized by optimal treatment. Characteristically, tubercle bacilli are slowly disposed of or killed by the body after the best available chemotherapy. The widespread use of isoniazid for example has been accompanied by the development of resistant strains with the result that current drugs may fail to eradicate the mycobacterial infections. It is therefore important to develop new drugs with different mechanisms of antimycobacterial action. However, these agents need not be those associated with highest potency on a dosage basis for general utility.

Optimal antituberculous therapy requires the use of several drugs in combination from the outset of therapy. Mycobacterial populations contain some spontaneous mutants which are resistant to drugs even prior to exposure. The frequency of such mutations can vary between 1 in less than 100 to 1 in greater than 10,000, depending upon the drug. Single drug therapy can inhibit the majority of organisms in an infected site, yet permit, and in fact encourage, uncontrolled growth of the resistant mutants. Early combination therapy with at least two drugs is the preferable method of preventing emergence of large resistant populations in the original tuberculous cavities. (Antimycobacterial agents are discussed at length in *Medicinal Chemistry*, Part I, Alfred Burger, ed. (Wiley-Interscience, N.Y. 1970), Chapter 19.)

Some therapeutic agents are most valuable for their ability to suppress emergence of resistance during combination therapy. An example is p-aminosalicylic acid, which can delay development of streptomycin resistance. See Burger, p. 429. Thus, anti-mycobacterial agents can be important not only for their own efficacy against susceptible organisms but for their ability to enhance effectiveness of other agents by controlling emergence of resistant populations, for example populations resistant to pyrazinamide, which is a major drug used in the therapy of tuberculosis. The synthesis of pyrazinamide was described by Kushner et al, J. Am. Chem. Soc. 74:3617 (1952), and the compound was patented in 1954 as a tuberculostatic agent. Williams, U.S. Pat. No. 2,677,641. When pyrazinamide is used alone resistance develops quickly, and for this reason it is usually administered in combination with other drugs such as isoniazid. Another disadvantage of pyrazinamide is its hepatotoxicity.

Although the precise mechanism of action of pyrazinamide is not known, it is hypothesized that the compound is acted upon by an amidase in the Mycobacterial cells, releasing pyrazinoic acid as the active component of the compound. Pyrazinamide is only active against *Mycobacterium (M.) tuberculosis*. It is not active against the closely related organism *M. bovis* or other mycobacteria.

It has been suggested that resistance to pyrazinamide is based on a decreased level of the nicotinamidase in resistant organisms. We hypothesized that if the level of the amidase was important in resistance to this compound, one might develop a series of pyrazinoic acid esters which would circumvent this mechanism of resistance because they would require an esterase rather than an amidase for their activation. Evaluation of several commercially available nicotinic acid esters suggested that pyrazinoic acid esters might be effective against pyrazinamide-resistant *M. tuberculosis* and *M. bovis*.

There is little or no support in the prior art for using pyrazinoic acid esters as tuberculostatic agents. U.S. Pat. No. 2,646,431 issued to Dalalian and Kushner covered pyrazine derivatives and methods of preparation. One such group of derivatives, thiolpyrazinoates, showed bacteriostatic and bacteriocidal properties against human tubercle bacillus. However, the specification states that in general, pyrazine monocarboxylic acid and derivatives such as esters do not possess bacteriostatic or bacteriocidal properties.

In 1954 Kushner et al, J. Am. Chem. Soc. 77:1152–1155, reported the use of ethyl mercaptan and related compounds in experimental treatment of tuberculosis. Isopropyl thiopyrazinoate applied subcutaneously exhibited activity in a standardized mouse test. However, the authors attributed this activity to the release of ethyl mercaptan, not to the pyrazinoyl residue. Brown et al, J. Am. Chem. Soc. 76:3860 (1954) also reported that ethyl mercapto compounds had antituberculosis activity, thus supporting the Kushner et al. assertion that the activity of ethyl thiolpyrazinoate was due to ethyl mercaptan and not the pyrazinoyl residue. The only suggestion that pyrazinoic acid esters might have some value in tuberculosis therapy is found in Solomons and Spoerri, J. Am. Chem. Soc. 75:679 (1953). In the course of evaluating esters of pyrazinoic and pyrazine-2,3-dicarboxylic acids as local anaesthetics, the authors learned of the effectiveness of pyrazinamide as a tuberculostatic agent. The authors tested their anaesthetic compounds for in vitro activity against *Mycobacterium tuberculosis* H37RV and reported that a few were active, including N,N-dimethyl-2-aminoethyl pyrazinoate. No further work appears to have been done with this compound, however. In addition, effectiveness against other mycobacteria, including pyrazinamide-resistant *M. tuberculosis*, would not have been obvious on the basis of this isolated in vitro test.

In 1958, Suzuki et al, Takamine Kenkyusho Nempo 10:19–23, reported that the pyrazinoate ester of chloramphenicol was inactive against a number of bacteria including *M. tuberculosis*.

Summary

The synthesis of pyrazinoic acid esters and their use against a variety of mycobacteria is disclosed. Compounds of this group are effective against *M. tuberculo-* sis, pyrazinamide-resistant *M. tuberculosis, M. kansasii,* and *M. bovis.*

DETAILED DESCRIPTION OF THE INVENTION

The present invention relates to novel compositions comprising compounds of the formula:

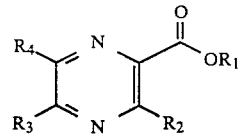

or a pharmaceutically acceptable salt thereof having anti-mycobacterium bovis, anti-mycobacterium tuberculosis or anti-nycobacterium kansasii activity and a pharmaceutically acceptable carrier wherein:

$R_1$ is
  (a) lower alkyl, especially $C_{2-6}$ alkyl such as n-propyl, n-butyl, i-pentyl, n-pentyl and n-hexyl;
  (b) lower haloalkyl, especially fluoro, chloro or bromo $C_{2-6}$ alkyl such as bromoethyl, chloroethyl and trifluoroethyl;
  (c) lower cycloalkyl, especially $C_{3-6}$ cycloalkyl, e.g. cyclopropyl, cyclopentyl and cyclohexyl;
  (d) lower alkenyl, especially $C_{2-6}$ alkenyl such as 2-propenyl and 2-butenyl;
  (e) lower alkynyl, especially $C_{2-6}$ alkynyl such as 2-propynyl and 2-butynyl;
  (f) aryl especially $C_{6-13}$ aryl, e.g.; phenyl, biphenyl or substituted phenyl of the formula:

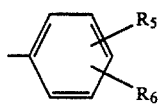

wherein $R_5$ and $R_6$ independently are
  (1) Q, where Q is H, lower alkyl, especially $C_{1-6}$ alkyl, lower haloalkyl, especially fluoro $C_{1-6}$ alkyl, such as trifluoromethyl, phenyl or substituted phenyl;
  (2) halo, such as fluoro, chloro or bromo;
  (3) nitro;
  (4) OQ; or
  (5) SQ;
  (g) benzyl or substituted benzyl of formula

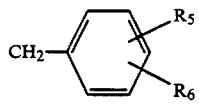

wherein $R_5$ and $R_6$ are as previously defined.
$R_2$ is
  (a) H; or
  (b) halo, especially fluoro, chloro or bromo; $R_3$ and $R_4$ independently are:
  (a) H;
  (b) halo, especially fluoro, chloro or bromo;
  (c) lower haloalkyl, especially fluoro $C_{1-6}$ alkyl, such as trifluoromethyl;
  (d) OQ; or
  (e) SQ Preferably an antimycobacterial agent of this invention is of the formula:

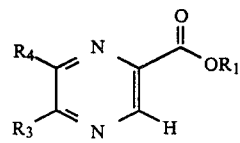

wherein $R_1$, $R_3$, $R_4$, $R_5$, and $R_6$ are as previously defined.

More preferably an antimycobacterial agent of this invention is of the formula:

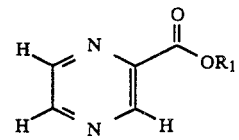

wherein
$R_1$ is
  (a) lower alkyl;
  (b) lower haloalkyl;
  (c) lower alkenyl; or
  (d) aryl, especially substituted phenyl wherein $R_5$ and $R_6$ are Q.

Preparation of the compounds of the invention

The compounds of the present invention are prepared from known starting materials via various procedures, for example, the method described below:

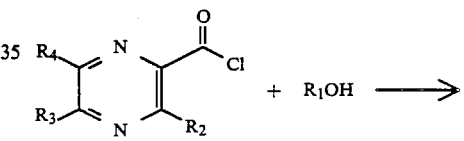

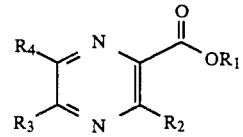

By this method an appropriately functionalized pyrazinoic acid is condensed via the formation of the pyrazinoic acid chloride with an alcohol to yield the desired esters.

Utility of the compounds within the scope of the invention

The pharmaceutical compositions containing the active ingredient may be in a form suitable for oral use, for example as tablets, aqueous or oily suspensions, dispersible powders or granules, emulsions, hard or soft capsules. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets may contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example corn starch or alginic acid; binding agents, for example, starch, gelatin or acacia, and lubricating agents, for example magnesium stearate, stearic acid or talc. The tablets may be uncoated or they may be coated by known techniques to delay disintegration and absorption in the gastrointestinal tract and thereby provide sustained action over a longer period.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example peanut oil, liquid paraffin, or olive oil.

Aqueous suspensions contain the active materials in admixture with excipients suitable for the manufacture of aqueous suspensions. Such excipients are suspending agents, for example sodium carboxymethylcellulose, methylcelluose, hydroxypropylmethylcellulose, sodium alginate, polyvinylpyrrolidone, gum tragacanth, and gum acacia; dispersing or wetting agents may be a naturally-occurring phosphatide, for example lecithin or condensation products of alkylene oxide with fatty acids, for example polyoxyethylene stearate, or condensation products of ethylene oxide with long chain aliphatic alcohols, for example heptadecethyleneoxycetanol, or condensation products of ethylene oxide with partial ester derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl, p-hydroxybenzoate, one or more coloring agents, one or more flavoring agents, and one or more sweetening agents such as sucrose or saccharin.

Oily suspensions may be formulated by suspending the active ingredient in a vegetable oil, for example such as arachis oil, olive oil, sesame oil or coconut oil, or in a mineral oil such as liquid paraffin. The oil suspensions may contain thickening agent, for example beeswax, hard paraffin or cetyl alcohol. Sweetening agents such as those set forth above, and flavoring agents may be added to provide a palatable oral preparation. These compositions may be preserved by addition of an antioxidant such as ascorbic acid. Dispersible powders and granules suitable for preparation of an aqueous suspension by the addition of water provide the active ingredient in admixture with a dispersing or wetting agent, a suspending agent and one or more preservatives. Suitable dispersing or wetting agents and suspending agents are exemplified by those already mentioned above. Additional excipients, for example sweetening, flavoring and coloring agents, may also be present. The pharmaceutical compositions of the invention may also be in the form of oil-in-water emulsions. The oily phase may be a vegetable oil, for example olive oil or arachis oil, or a mineral oil, for example liquid paraffin or mixtures of these. Suitable emulsifying agents may be naturally-occurring gums, for example gum acacia or gum tragacanth, naturally-occurring phosphatides, for example soy bean, lecithin, and esters or partial esters derived from fatty acids and hexitol anhydrides, for example sorbitan monooleate, and condensation products of the said partial esters with ethylene oxide, for example polyoxyethylene sorbitan monooleates. The emulsions may also contain sweetening and flavoring agents.

Syrups and elixirs may be formulated with sweetening agents, for example glycerol, propylene glycol, sorbitol or sucrose. Such formulations may also contain a demulcent, a preservative and flavoring and coloring agents. The pharmaceutical compositions may be in the form of a sterile injectable aqueous or oleagenous suspension. The suspension may be formulated according to the known art using those suitable dispersing and wetting agents and suspending agents which have been mentioned above. The sterile injectable preparation may also be a sterile injectable solution or suspension in a non-toxic parenterally-acceptable diluent or solvent, for example as a solution in 1,3-butanediol. Among acceptable vehicles and solvents that may be employed are water, Ringer's solution, and isotonic sodium chloride solution. In addition, sterile, fixed oils are conventionally employed as a solvent or suspending medium. For this purpose any bland fixed oil may be employed including synthetic mono- or-diglycerides. In addition fatty acids such as oleic acid find use in the preparation of injectibles.

Biological Data supporting the Utility of the Compounds Within the Scope of the Invention 1. Methods employed for biological evaluation of the compounds were modified from Vestal, A. L. Procedures for isolation and identification of mycobacteria, P.H.S. Publication No. 1995, Laboratory Division, National Communicable Disease Center, Atlanta, Ga., 1969. Stock solutions of each pyrazinoic acid ester were prepared by hydrating a known weight of the agent in water or DMSO. The stock solutions were sterilized by passage through a 0.2 μm nylon membrane filters. Compartmented plates were prepared with serial 2-fold dilutions (200 μg/ml to 3 μg/ml) of the various compounds in Middlebrook 7H10 agar with oleic acid, dextrose, catalase, (OADC) enrichment at pH 5.8 (testing at pH 5.6 would yield a lower minimum inhibitory concentration (MIC), but M. bovis does not grow well at that pH).

Mycobacteria were grown in Middlebrook 7H10 broth with OADC enrichment and 0.05% Tween 80 at pH 6.6. A Klett-Summerson colorimeter was used to standardize the cell suspensions using 7H10 broth as the diluent. Ten microliters of each cell suspension (1 Klett, 0.2 Klett and 0.1 Klett) yielding approximately $5\times10^3$ CFU, $10^3$ CFU and $5\times10^2$ CFU was spotted on each compartment. A control compartment, having no drug, was used for each isolate. All plates were incubated at 37° C. for 4–6 weeks. The MIC is defined as the lowest concentration of drug which produced a 99% (2 log) inhibition of growth.

2. Biological utility of the compounds. The above mentioned compounds are active against clinical isolates of *M. tuberculosis, M. bovis,* and *M. kansasii.* In addition, these compounds are active against pyrazinamide resistant isolates of *M. tuberculosis.* See Tables 1–4.

TABLE 1

Effect of β, β, β-Trifluoroethyl Pyrazinoate on Mycobacteria

| Organism[2] | MIC[1] |
|---|---|
| M. kans. SWK | 200 |
| M. kans. SCH | 100 |
| BCG GLX | 200 |

TABLE 1-continued
Effect of β, β, β-Trifluoroethyl Pyrazinoate on Mycobacteria

| Organism[2] | MIC[1] |
|---|---|
| BCG ILL | 200 |
| M. tb. PZA ®1 | 50 |
| M. tb. PZA ®2 | 50 |
| M. tb. PZA ®3 | 50 |
| M. tb. BUR | 25 |
| M. tb. CES | 12.5 |
| M. tb. DOL | 25 |
| M. tb. SMA | 25 |
| M. tb. MUT[1] | 200 |
| M. tb. MUT[2] | 25 |
| M. tb. MUT[3] | 25 |
| M. tb. DUB | 25 |
| M. tb. GLA | 12.5 |
| M. tb. ING | 25 |
| M. tb. LFL | 50 |
| M. tb. MCQ | 25 |
| M. tb. WOO | 25 |
| M. tb. 311 | 25 |
| M. tb. BAK | 25 |
| M. tb. DOU | 100 |

[1] MIC (Minimum Inhibitory Concentration) is the lowest concentration of substance in μg/mL which produced a 99% (2 log) inhibition of growth. >200 μg/mL of pyrazinamide was required to achieve a 99% inhibition of growth of *M. tuberculosis* (PZA ®, MUT, and 311) and *M. bovis* (BCG GLX and ILL).

2. Abbreviations used in Tables

BCG: Bacillus Calmette-Guerin, an attenuated *Mycobacterium bovis*.

M. tb. PZA[R]: *Mycobacterium tuberculosis* (laboratory mutant, nitrosoguanidine induced, resistant to pyrazinamide).

M. tb. MUT: *Mycobacterium tuberculosis* (laboratory mutant, nitrosoguanidine induced, resistant to pyrazinoic acid.)

M. tb. 311: *Mycobacterium tuberculosis* (laboratory mutant from the Trudeau collection, resistant to pyrazinamide).

Unless indicated otherwise, the remaining abbreviations refer to clinical isolates, for example *M. Kans.* SWK: *Mycobacterium kansasii* (isolated from patient SWK).

TABLE 2
Effect of Allyl Pyrazinoate on Mycobacteria

| Organism | MIC |
|---|---|
| M. kans. SWK | 6.25 |
| M. kans. SCH | 6.25 |
| BCG GLZ | 100 |
| BCG ILL | 100 |
| M. tb. PZA ®1 | 3.12 |
| M. tb. PZA ®2 | 12.5 |
| M. tb. PZA ®3 | 6.25 |
| M. tb. BUR | 6.25 |
| M. tb. CES | ≦3.12 |
| M. tb. DOL | ≦3.12 |
| M. tb. SMA | 3.12 |
| M. tb. MUT[1] | 6.25 |
| M. tb. MUT[2] | 3.12 |
| M. tb. MUT[3] | ≦3.12 |
| M. tb. DUB | 6.25 |
| M. tb. GLA | 6.25 |
| M. tb. ING | 3.12 |
| M. tb. LFL | 3.12 |
| M. tb. MCQ | ≦3.12 |
| M. tb. WOO | 6.25 |
| M. tb. 311 | 6.25 |
| M. tb. BAK | 3.12 |
| M. tb DOU | 3.12 |

TABLE 3
Effect of n-Propyl Pyrazinoate on Mycobacteria

| Organism | MIC |
|---|---|
| M. kans. SWK | 6.25 |
| M. kans. SCH | 12.5 |
| BCG GLX | >200 |
| BCG ILL | 200 |
| M. tb. PZA ®1 | 12.5 |
| M. tb. PZA ®2 | 12.5 |
| M. tb. PZA ®3 | 6.25 |
| M. tb. BUR | ≦3.12 |
| M. tb. CES | ≦3.12 |
| M. tb. DOL | ≦3.12 |
| M. tb. SMA | ≦3.12 |
| M. tb. MUT[1] | 25 |
| M. tb. MUT[2] | ≦3.12 |
| M. tb. MUT[3] | ≦3.12 |
| M. tb. DUB | ≦3.12 |
| M. tb. GLA | 6.25 |
| M. tb. ING | ≦3.12 |
| M. tb. LFL | 6.25 |
| M. tb. MCQ | ≦3.12 |
| M. tb. WOO | — |
| M. tb. 311 | 6.25 |
| M. tb. BAK | ≦3.12 |
| M. tb. DOU | ≦3.12 |

TABLE 4
Effect of p-Tolyl Pyrazinoate on Mycobacteria

| Organism | MIC |
|---|---|
| M. kans. SWK | 12.5 |
| M. kans. SCH | 12.5 |
| BCG GLX | 25 |
| BCG ILL | 50 |
| M. tb. PZA ®1 | 12.5 |
| M. tb. PZA ®2 | 25 |
| M. tb. PZA ®3 | 12.5 |
| M. tb. BUR | 12.5 |
| M. tb. CES | 12.5 |
| M. tb. DOL | 6.25 |
| M. tb. SMA | 25 |
| M. tb. MUT[1] | 12.5 |
| M. tb. MUT[2] | 12.5 |
| M. tb. MUT[3] | 6.25 |
| M. tb. DUB | 25 |
| M. tb. GLA | 6.25 |
| M. tb. ING | 25 |
| M. tb. LFL | 12.5 |
| M. tb. MCQ | 6.25 |
| M. tb. WOO | 25 |
| M. tb. 311 | 12.5 |
| M. tb. BAK | 12.5 |
| M. tb. DOU | 25 |

The following examples are offered for illustration and not by way of limitation.

EXAMPLE 1

β, β, α-Trifluoroethyl Pyrazinoate

Pyrazinecarboxylic acid (3.7 g, 30 mmol), benzene (25 mL) and thionyl chloride (15 mL) were added into a 100 mL round bottom flask. The reaction mixture was heated under reflux for two hours after which time benzene and excess thionyl chloride were removed by distillation. The dark red crude pyrazinoyl chloride was purified by sublimation under vacuum at a bath temperature of 50°–60° C. to give colorless crystals that weighed 3.2 g (74% yield). The purified pyrazinoyl chloride was transferred into a 100 mL flask containing 40 mL methylene chloride and 2 mL pyridine. The solution was cooled to 0° C. in an ice-bath and β, β, β-trifluoroethanol (2.4 g, 24 mmol) was added. The reaction mixture was stirred at 0° C. for one hour, warmed to room temperature slowly and then stirred at room temperature overnight. The reaction mixture was transferred to a 125 mL separatory funnel and washed with aqueous copper sulfate solution (2×20 mL) followed by water (20 mL) and brine solution (2×20 mL). The methylene chloride layer was then dried over magnesium sulfate and solvent evaporated. The residue was purified further by recrystallization from hexanes to give the title compound as colorless needles weighing 3.6 g (79% yield); m. p. 46°–48° C. Elemental Analysis: $C_7H_5F_3N_2O_2$ Calcd. C: 40.79, H: 2.45. Found: C: 40.96, H: 2.38.

EXAMPLE 2

(4-t-Butylphenyl) Pyrazinoate

The pyrazinoyl chloride was prepared as mentioned above from pyrazinecarboxylic acid (1.8 g, 15 mmol), benzene (11 mL) and thionyl chloride (7 mL) to give 1.62 g (75% yield) of the corresponding acid chloride. To the acid chloride dissolved in pyridine (2 mL) and methylene chloride (20 mL) cooled to 0° C. in a 50 mL round bottom flask was added 4-t-butylphenol (2.25 g, 15 mmol ). Upon completion of the reaction and isolation as described above recrystallization from hexanes yielded 2.1 g (72% yield) of the crystalline title compound; m.p. 89°–90° C. Elemental Analysis: $C_{15}H_{16}N_2O_2$ Calcd: C: 70.29, H: 6.29, Found: C: 70.55, H: 6.29.

EXAMPLE 3 p-Biphenyl Pyrazinoate

To 3.5 g (25 mmol) of pyrazinoyl chloride dissolved in methylene chloride (20 mL) and pyridine (2 mL) cooled to 0° C. in a 50 mL round bottom flask was added 4-phenyl-phenol (5.0 g, 30 mmol). Upon completion of the reaction and isolation as described above recrystallization from hexanes yielded 3.15 g (39% yield) of the crystalline title compound; m.p: 95°–98° C. Elemental Analysis: $C_{17}H_{12}N_2O_2$ Calcd: C:73.90, H:4.38. Found: C:73.68, H:4.28.

EXAMPLE 4 n-Propyl Pyrazinoate

To 4.0 g (28 mmol) of pyrazinoyl chloride dissolved in methylene chloride (20 mL) and pyridine (2 mL) cooled to 0° C. in a 50 mL round bottom flask was added n-propyl alcohol (4.0 g, 66 mmol). Completion of the reaction and separation as described above, followed by distillation, led to isolation of the title compound as a water white oil; b.p: 68°–73° C. at 0.20 mm Hg.

Elemental Analysis: $C_8H_{10}N_2O_2$ Calcd: C:57.82, H:6.07, Found: C:57.74, H:6.02.

EXAMPLE 5 p-Tolyl Pyrazinoate

To 3.5 g (25 mmol) of pyrazinoyl chloride dissolved in methylene chloride (20 mL) and pyridine (2 mL) cooled to 0° C. in a 50 mL round bottom flask was added 4-methyl-phenol (3.2 g, 30 mmol). Upon completion of the reaction and isolation as described above, recrystallization from hexanes yielded 1.51 g (24% yield) of the crystalline title compound; m.p.: 120°–123° C. Elemental Analysis: $C_{12}H_{10}N_2O_2$ Calcd: C:67.28, H:4.71. Found: C:67.4, H:4.66.

EXAMPLE 6

Allyl Pyrazinoate

To 4.0 g (28 mmol) of pyrazinoyl chloride dissolved in methylene chloride (20 mL) and pyridine (2 mL) at 0° C. in a 50 mL round bottom flask was added allyl alcohol (2.6 g, 45 mmol). Completion of the reaction and isolation as described above followed by distillation led to isolation of the title compound as a water white oil; b.p: 72°–74° C. at 0.25 mm Hg.

What is claimed is:

1. A composition comprising a compound of formula I or a pharmaceutically acceptable salt thereof having anti-myco bacterium bovis, anti-mycobacterium tuberculosis or anti-mycobacterium kansasii activity and a pharmaceutically acceptable carrier:

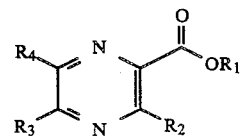

wherein: $R_1$ is (e) SQ.

2. A composition according to claim 1 wherein $R_1$ is a $C_{2-6}$ alkyl.

3. A composition according to claim 1 wherein $R_1$ is selected from the group consisting of n-propyl, n-butyl, i-pentyl, n-pentyl and n-hexyl.

4. A composition according to claim 1 wherein $R_1$ comprises a fluoro $C_{2-6}$ alkyl, chloro $C_{2-6}$ alkyl or bromo $C_{2-6}$ alkyl.

5. A composition according to claim 1 wherein $R_1$ is selected from the group consisting of bromoethyl, chloroethyl and trifluoroethyl.

6. A composition according to claim 1 wherein $R_1$ is a $C_{3-6}$ cycloalkyl.

7. A composition according to claim 1 wherein $R_1$ is selected from the group consisting of cyclopropyl, cyclopentyl and cyclohexyl.

8. A composition according to claim 1 wherein $R_1$ is a $C_{2-6}$ alkenyl.

9. A composition according to claim 1 wherein $R_1$ is selected from the group consisting of 2-propenyl and 2-butenyl.

10. A composition according to claim 1 wherein $R_1$ is a $C_{2-6}$ alkynyl.

11. A composition according to claim 1 wherein $R_1$ is selected from the group consisting of 2-propynyl and 2-butynyl.

12. A composition according to claim 1 wherein $R_1$ comprises a $C_{6-13}$ aryl.

13. A composition according to claim 1 wherein Q is selected from the group consisting of a $C_{1-6}$ alkyl and a fluoro $C_{1-6}$ alkyl.

14. A composition according to claim 1 wherein Q is selected from a group consisting of trifluoromethyl, phenyl and substituted phenyl of formula II.

15. A composition according to claim 1 wherein the halo of $R_5$ and $R_6$ is selected from the group consisting of fluoro, chloro and bromo.

16. A composition according to claim 1 wherein $R_2$ is fluoro, chloro or bromo.

17. A composition according to claim 1 wherein the halo of $R_3$ and $R_4$ is fluoro, chloro or bromo.

18. A composition according to claim 1 wherein the lower haloalkyl of $R_3$ and $R_4$ is fluoro $C_{1-6}$ alkyl.

19. A composition according to claim 1 wherein the lower haloalkyl of $R_3$ and $R_4$ is trifluoromethyl.

20. A composition comprising a compound having anti-mycobacterium tuberculosis, anti-mycobacterium bovis or anti-mycobacterium kansasii activity selected from the group consisting of β, β, β-trifluoromethyl pyrazinoate, 4-t-butylphenyl pyrazinoate, p-biphenyl pyrazinoate, n-propyl pyrazinoate, β-chloroethyl pyrazinoate and allyl pyrazinoate, or a pharmaceutically acceptable salt thereof; and a pharmaceutically acceptable carrier.

21. A composition according to claim 1 wherein an effective amount of the compound of formula I or pharmaceutically acceptable salt thereof is provided.

22. A composition according to claim 20 wherein an effective amount of the compound of formula I or pharmaceutically acceptable salt thereof is provided.

23. A method of treating a mammal infected with *Mycobacterium bovis, Mycobacterium tuberculosis* or *Mycobacterium kansasii* comprising administering to the mammal a non-toxic effective amount of the compound of formula I or a pharmaceutically acceptable salt thereof having anti-mycobacterium bovis, anti-mycobacterium tuberculosis or anti-mycobacterium kansasii activity and a pharmaceutically acceptable carrier:

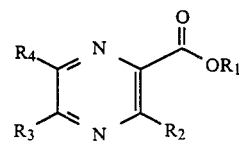

wherein $R_1$ is
(a) a lower alkyl;
(b) a lower haloalkyl;
(c) a lower cycloalkyl;
(d) a lower alkenyl;
(e) a lower alkynyl;
(f) a phenyl, biphenyl or substituted phenyl of the formula II;

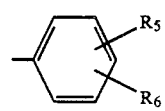

wherein $R_5$ and $R_6$ independently are
(1) Q, where Q is H, lower alkyl, or lower haloalkyl;
(2) halo;
(3) nitro;
(4) OQ; or
(5) SQ; or
(g) a benzyl or substituted benzyl or formula:

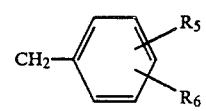

wherein $R_5$ and $R_6$ independently are
(1) Q, where Q is H, lower alkyl, or lower haloalkyl;
(2) halo;
(3) nitro;
(4) OQ; or
(5) SQ;
$R_2$ is
(a) H; or
(b) halo; and
$R_3$ and $R_4$ independently are
(a) H;
(b) halo;
(c) lower haloalkyl;
(d) OQ; or
(e) SQ.

24. A method of treating a mammal infected with *Mycobacterium bovis, mycobacterium tuberculosis* or *Mycobacterium kansasii* comprising administering to the mammal a non-toxic effective amount of a compound having anti-mycobacterium tuberculosis, anti-mycobacterium bovis or anti-mycobacterium kansasii activity selected from the group consisting of β, β, β-trifluoroethyl pyrazinoate, 4-t-butylphenyl pyrazinoate, p-biphenyl pyrazinoate, n-propyl pyrazinoate, β-chloroethyl pyrazinoate and allyl pyrazinoate, or a pharmaceutically acceptable salt thereof and a pharmaceutically acceptable carrier.

* * * * *